United States Patent [19]

Miller

[11] Patent Number: 4,565,654

[45] Date of Patent: Jan. 21, 1986

[54] N-ACYLOXY MONOCYCLIC β-LACTAMS

[75] Inventor: Marvin J. Miller, South Bend, Ind.

[73] Assignee: University of Notre Dame Du Lac, Notre Dame, Ind.

[21] Appl. No.: 479,375

[22] Filed: Mar. 28, 1983

[51] Int. Cl.[4] .......................................... C07D 411/12
[52] U.S. Cl. .............................. 260/239 A; 260/245.4; 260/330.3; 260/330.9
[58] Field of Search .............. 260/239 A, 245.4, 330.3, 260/330.9

[56] References Cited

U.S. PATENT DOCUMENTS 4,337,197  6/1982  Gordon ........................... 260/239 A
4,386,034  5/1983  Floyd et al. ..................... 260/456 A

OTHER PUBLICATIONS

Miller et al., J. Amer. Chem. Soc. 102, 7030 (1980).
Mattingly et al., Chem. Abs. 94, 197018x (1981).
Miller et al. II, Tetrahedron 39, 2571-75 (1983).
D. M. Floyd et al., "Monobactams. Preparation of (S)-3-Amino-2-Oxoazetidine-1-Sulfonic Acids from L-α-Amino-β-Hydroxy Acids via Their Hydroxamic Esters", J. Org. Chem. 1982, 47, 5160-5167.
D. M. Floyd et al., "Monobactams. Stereospecific Synthesis of (S)-3-Amino-2-Oxoazetidine-1-Sulfonic Acids", J. Org. Chem., 1982, 47, 176-178.

Primary Examiner—Mark L. Berch
Attorney, Agent, or Firm—William B. Scanlon; Arthur R. Whale

[57] ABSTRACT

Process for N-acyloxy or sulfooxy 2-azetidinones comprising O-acylation of a β-hydroxy or β-halo hydroxamic acid, and cyclizing the O-acylhydroxamate with TPP-CCl$_4$-TEA or with TPP-dialkylazodicarboxylate to the N-acyloxy-2-azetidinone. Solvolysis of the acyl group provides an N-hydroxy-2-azetidinone. E.g., N-Cbz-L-serine is converted to the O-acetyl hydroxamate, cyclized and solvolyzed to N-hydroxy-3-(Cbz-amino)-2-azetidinone. The N-hydroxy-2-azetidinones are useful intermediates to monocyclic β-lactam antibiotics and β-lactamase inhibitors.

12 Claims, No Drawings

N-ACYLOXY MONOCYCLIC β-LACTAMS

The invention described herein was made in the course of work under a grant or award from the Department of Health and Human Services.

BACKGROUND OF THE INVENTION

This invention relates to a process for the production of monocyclic β-lactams and to intermediates employed in the process. In particular, it relates to a process for the production of N-hydroxy-2-azetidinones, intermediates which can be converted by known methods to N-unsubstituted azetidinones or to O-sulfated N-hydroxy-2-azetidinones.

The recent discovery and structure elucidation of the β-lactamase inhibitor clavulanic acid, the antibiotic penems and carbapenems, as well as the monocyclic nocardicins and monobactams have led to a reconsideration of the structure-activity relationships of the β-lactam antibiotics. Consequently, related synthetic and enzymatic studies of monocyclic β-lactams have received new impetus. This invention provides a simple and economically practical method for the production of N-hydroxy-2-azetidinones which are key intermediates for the preparation of monocyclic β-lactams, including the nocardicins, monobactams, and the newer O-sulfated N-hydroxy-2-azetidinone antibiotics.

SUMMARY OF THE INVENTION

β-Substituted-esters are reacted with hydroxylamine to provide the O-unsubstituted hydroxamic acids. The hydroxamic acids are acylated or sulfated to provide the O-acyl or O-sulfohydroxamates and the latter are cyclized to 1-acyloxy- or 1-sulfooxy-2-azetidinones. The N-acyloxyazetidinones are subjected to solvolysis to provide N-hydroxy-2-azetidinones. Preferably, amino-protected β-substituted-α-amino acid esters are converted to N-hydroxy-3-protected-amino-2-azetidinones which are useful intermediates. The O-sulfo N-hydroxyazetidinones are useful intermediates to antibiotics.

The N-hydroxyazetidinones can be converted by known methods to nocardicin-type antibiotics, monobactams, O-sulfated azetidinones, penem, and carbapenem compounds.

DETAILED DESCRIPTION

According to the process of this invention, a β-substituted acid ester represented by the formula 1

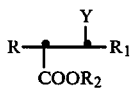
COOR$_2$   1 is reacted with hydroxylamine to provide the hydroxamic acid derivative represented by the formula 2

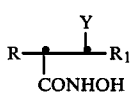
CONHOH   2

The hydroxamic acid 2 is acylated with an active derivative of a carboxylic acid or with pyridine-SO$_3$ to an O-acylhydroxamate or O-sulfohydroxamate represented by the formula 3

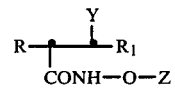
CONH—O—Z   3 wherein Z represents an acyl group or sulfo group, and Y is hydroxy, chloro, or bromo.

The O-acyl or O-sulfohydroxamate is cyclized to the O-acyl N-hydroxyazetidinone or O-sulfo N-hydroxyazetidinone represented by the formula 4. When Y is hydroxy, the cyclization is carried out with a dialkylazodicarboxylate and an organo phosphorus compound selected from triphenylphosphine, triphenylphosphite, diphenyl phenylphosphonate, and phenyldiphenylphosphinoate. When Y is chloro or bromo, the cyclization is carried out with a base.

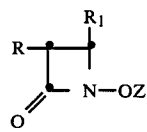
4

In the above formulae 1–4, R is a protected amino group, hydrogen, C$_1$–C$_4$ alkyl, C$_1$–C$_4$ alkoxycarbonyl, protected carboxy, or C$_1$–C$_4$ alkyl substituted by hydroxy, halogen, methoxy, protected amino, protected carboxy, or cyano.

R$_1$ represents hydrogen, C$_1$–C$_4$ alkyl, C$_1$–C$_4$ alkoxycarbonyl, protected carboxy, phenyl, or substituted phenyl substituted by C$_1$–C$_4$ alkyl, hydroxy, halogen, C$_1$–C$_4$ alkoxy, protected amino, protected carboxy, or cyano; or R$_1$ is C$_1$–C$_4$ alkyl substituted by hydroxy, halogen, methoxy, protected amino, protected carboxy, or cyano.

R$_2$ represents C$_1$–C$_4$ alkyl, or a carboxy protecting group; and Z represents an acyl group

wherein R$_3$ is C$_1$–C$_{10}$ alkyl, C$_2$–C$_{10}$ alkenyl, C$_2$–C$_{10}$ alkinyl, phenyl, substituted phenyl substituted by C$_1$–C$_4$ alkyl, C$_1$–C$_4$ alkoxy, halogen, or nitro; C$_1$–C$_{10}$ alkyl substituted by halogen, C$_1$–C$_4$ alkoxycarbonyl, C$_1$–C$_4$ alkylsulfonyl, nitro, C$_1$–C$_4$ alkoxy, phenyl or substituted phenyl as defined above; or Z is a sulfo group represented by the formula —SO$_3^-$M$^+$, wherein M$^+$ is an alkali metal cation, pyridinium, ammonium, or a tri or tetraalkyl ammonium ion.

The term protected carboxy as used in the above formulae refers to the carboxy group blocked or protected by a group which is readily removable by hydrolysis or hydrogenolysis. Such groups are well known as conventional carboxy-protecting groups commonly used in the β-lactam art for the temporary protection or blocking of the acidic, reactive carboxy group. These protecting groups function to block the participation of the carboxy group in reactions directed at other sites or functional groups in the molecule. For example, during the acylation of the O-acyl hydroxamates a carboxy group R or R$_1$ is desirably protected. Examples of such protecting groups are t-butyl, trihaloethyl eg. 2,2,2-trichloroethyl, 2-iodoethyl, allyl, benzyl, p-methoxybenzyl, p-nitrobenzyl, and diphenylmethyl.

When in the above formulae $M^+$ is a tri or tetraalkylammonium ion ($Z=SO_3^-M^+$), $M^+$ can be a tri-($C_1$-$C_4$ alkyl)ammonium ion such as triethylammonium or tributylammonium, or a tetra($C_1$-$C_4$ alkyl)ammonium ion such as tetra-n-butylammonium, or a di- or trialkyl benzylammonium ion such as benzyl triethylammonium.

The O-acylhydroxamates (3, Z=acyl) are prepared by the acylation of the hydroxamic acid (2) with an active derivative of the carboxylic acid $R_3COOH$. Active derivatives of the carboxylic acid which are useful in the acylation include the acid anhydrides and acid halides. Acid halides eg., the acid chlorides and acid bromides, are used in the acylation in the presence of an acid-binding agent such as the tertiary amines triethylamine, N,N-diethylaniline and like amines. Preferably, the O-acylhydroxamates (3) are prepared with the acid anhydrides.

Examples of carboxylic acids $R_3COOH$ which can be used in the acylation are acetic acid, propionic acid, butyric acid, isobutyric acid, valeric acid, caproic acid, pelargonic acid, acrylic acid, vinylacetic acid, propiolic acid, trimethylacetic acid, methoxyacetic acid, methoxypropionic acid, benzoic acid, anisic acid, p-nitrobenzoic acid, 3-methoxybenzoic acid, p-chlorobenzoic acid, toluic acid, phenylacetic acid, 4-phenylbutyric acid, butenoic acid, butynoic acid, and hexynoic acid.

A preferred carboxylic acid is a lower alkyl carboxylic acid, especially acetic acid. Another preferred acid is benzoic acid or a substituted benzoic acid.

The O-sulfo hydroxamates (formula 3, $Z=SO_3^-M^+$) are prepared with the hydroxamic acid (2) and pyridine-sulfur trioxide complex. The reaction is carried out by mixing the hydroxamic acid with the pyridine-$SO_3$ complex in an inert solvent preferably pyridine. The pyridine-$SO_3$ complex is commercially available or can be prepared by dissolving the desired amount of sulfur trioxide in excess pyridine. The pyridine solution of the complex is then added to a solution of the hydroxamic acid in an inert solvent. Alternatively, sulfur trioxide can be added to a solution of the hydroxamic acid in pyridine or in an inert solvent containing pyridine.

The acylation or O-sulfo formation is carried out with the hydroxamic acid (2) at ordinary room temperatures in an inert solvent with an excess of the acylating agent or pyridine-$SO_3$ complex. The reaction proceeds well at a temperature between about 15° C. and about 45° C. and proceeds at a convenient rate at about 20° C. to about 25° C.

The acid halide, acid anhydride or active ester of the $R_3$—COOH acid is added in excess of the stoichiometric amount and generally a 2-3 fold excess is desirable for most practical acylating moieties.

Inert solvents useful in the process include for example, methyl alcohol, ethyl alcohol, tetrahydrofuran, acetonitrile, methylene chloride and like common organic solvents in which the hydroxamic acid (2) and the acylating agent is at least partially soluble.

The progress of the acylation or O-sulfo formation can be followed by thin layer chromatography or by using the ferric chloride color test on a small aliquot of the reaction mixture. The hydroxamic acid (2) is positive to ferric chloride (generally red color) while the acyl derivative is not. Upon completion of the reaction the test is negative.

In order to prevent premature solvolysis of the O-acyl derivatives (Z=acyl) prior to cyclization, the acylation reaction mixture is worked up promptly after completion. The product 3 is readily isolated by conventional procedures. In one such procedure the reaction mixture is poured into a mixture of dilute aqueous sodium or potassium carbonate and an organic solvent such as ethyl acetate. The product is taken up in the weakly basic solution which is mixed with an organic solvent such as methylene chloride or ethyl acetate and the mixture acidified to pH 4-5. The product is taken up by the organic layer which is separated, washed, dried and evaporated to provide the product (3).

The cyclization of 3, wherein Y is OH, to the azetidinone-2 ($\beta$-lactam 4) is carried out with a dialkylazodicarboxylate (DAAD) and an organo phosphorus compound selected from triphenylphosphine (TPP), triphenylphosphite, diphenyl phenylphosphonate $\phi$—P(O$\phi$)$_2$, and phenyl diphenylphosphinoate ($\phi$)$_2$P—O$\phi$, or with TPP-carbon tetrachloride-triethylamine. The cyclization step of the process is carried out under substantially anhydrous conditions in an inert solvent, eg. acetonitrile or tetrahydrofuran, at a temperature between about 15° C. and about 40° C. and, preferably, at about 20° C. to about 25° C. For best results the reaction is carried out in an atmosphere of a dry inert gas such as nitrogen or argon. The phosphorus compound and dialkylazodicarboxylate are each used in excess of 100 mole percent relative to compound 3. A preferred dialkylazodicarboxylate is diisopropylazodicarboxylate. Diethylazodicarboxylate also functions well in the cyclization; however, because of its lower cost the diisopropyl reagent is preferred for large scale manufacture. The preferred phosphorus compound is TPP.

Alternatively, the cyclization of 3 to 4 is carried out with triphenylphosphine-carbon tetrachloride and triethylamine (TPP-CCl$_4$-TEA). Each of the components of the reagent are used in excess of 100 mole percent relative to the O-acyl or O-sulfo derivative 3.

The N-acyloxy- or N-(O-sulfo)-2-azetidinone 4 is recovered from the reaction product mixture and purified by chromatography and recrystallization.

The reaction is carried out with the TPP-DAAD reagent as follows. The O-acyl or O-sulfohydroxamate 3 is dissolved in an inert dry solvent, eg. tetrahydrofuran, and with the solution protected from atmospheric moisture the TPP and DAAD are added. Alternatively, the O-acyl or O-sulfohydroxamate 3 or an anhydrous solution thereof is added to a dry solution of the TPP and DAAD. The mixture is stirred at room temperature and monitored by thin layer chromatography. When the reaction is completed, the mixture is concentrated by evaporation and the concentrate or residue containing the $\beta$-lactam product is purified by chromatography.

The cyclization of 3 with the TPP-CCl$_4$-TEA reagent is carried out as follows. An anhydrous solution of 3 and CCl$_4$ is prepared and protected from atmospheric moisture. The TPP and TEA are added and the reaction mixture is agitated with stirring or shaking. The reaction is monitored by thin layer chromatography and when complete, the product 4 is recovered and purified by chromatography and recrystallization. For example, when cyclization is complete the reaction mixture is concentrated by evaporation and the concentrate containing the product is chromatographed over silica gel.

The cyclization of an O-acyl or O-sulfohydroxamate (3), wherein R is an acylamino group as defined hereinafter, to an N-acyloxy or N-sulfooxyazetidinone-2 is preferably carried out with the TPP-DAAD reagent. However, when the amino-protecting group is a carbamate-forming type such as ethoxycarbonyl or benzyloxycarbonyl, the preferred cyclization reagent is TPP-CCl$_4$-TEA.

The cyclization of the O-acyl or O-sulfo hydroxamate 3 to the $\beta$-lactam 4 when Y is other than hydroxy is carried out with an organic or inorganic base. For example, the cyclization can be carried out with sodium hydride, a lithium alkylamide such as lithium diisopropylamide, and lithium di-tert-butylamide, or with an alkali metal carbonate such as lithium, sodium or potassium carbonate.

The cyclization is carried out under anhydrous conditions at a temperature between about $-15°$ C. and about $25°$ C. with a lithium dialkylamide or sodium hydride. When the base is an alkali metal carbonate, somewhat higher temperatures may be used eg. temperatures between about $15°$ C. and about $40°$ C.

The cyclization occurs readily owing to the acidity of the N-H proton of the O-acyl or O-sulfo hydroxamate 3.

In an example of the process, N-phthaloyl $\beta$-chloroalanine methyl ester is reacted with hydroxylamine and the hydroxamic acid is acylated with acetic anhydride to provide the compound represented by the formula 3, wherein R is phthalamido, Y is chloro, R$_1$ is hydrogen and Z is acetyl. The O-acetyl hydroxamate is then treated in dry tetrahydrofuran with lithium diisopropylamide to form the correspondingly substituted O-acetyl N-hydroxyazetidinone 4. Alternatively, the cyclization may be effected by shaking the THF solution of the O-acetyl hydroxamate with dry sodium carbonate.

The N-sulfooxy-2-azetidinones (4, Z=SO$_3$$^-$M$^+$) prepared in the process of this invention are useful in the preparation of antibiotics such as those disclosed in U.S. Pat. No. 4,337,197. The N-acyloxyazetidinones (4, Z=COR$_3$) are converted to N-hydroxyazetidinones by a further process provided by this invention. The N-hydroxy intermediates are useful in the preparation of monobactams and nocardicins.

According to this process the N-acyloxy-2-azetidinone (4) is subjected to mild solvolysis conditions to provide the N-hydroxy-2-azetidinone represented by the formula 5.

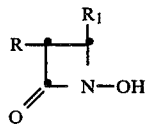

The solvolysis can be carried out under a variety of mild solvolytic conditions, eg. with aqueous sodium carbonate, aqueous potassium carbonate, aqueous ammonium acetate, aqueous ammonium carbonate, aqueous dimethylsulfoxide and sodium carbonate or potassium carbonate; and like reagents. A water miscible organic solvent may also be used with the above aqueous solutions. For example, methyl alcohol, ethyl alcohol, tetrahydrofuran, DMAC or DMF may be used to solubilize the N-acyloxy-2-azetidinone (4). Aqueous sodium carbonate at a concentration of about 3–5% and methyl alcohol is a convenient solvolytic medium. Another convenient solvolytic system comprises an aqueous solution of ammonium acetate (ca. 5%) and methyl alcohol or tetrahydrofuran. In general, the solvolysis is carried out in an aqueous organic solvent mixture at a pH of between about 8 and about 10.

The solvolysis is carried out at a temperature between about $0°$ C. and about $45°$ C. and preferably at about $0°$ C. to about $20°$ C. The solvolysis is conveniently carried out by adding solid sodium carbonate with vigorous agitation to a solution or suspension of the N-acyloxy-2-azetidinone. The progress of the solvolysis can be followed readily by thin layer chromatography. The N-hydroxy-2-azetidinone is recovered by adjusting the pH of the solvolysis mixture to about 5 and extracting the product with a water immiscible organic solvent such as ethyl acetate. The extract is washed, dried and evaporated to provide the N-hydroxy-2-azetidinone. The product can be further purified, if necessary, by recrystallization.

In carrying out the solvolysis reaction and in recovering the N-hydroxy product (5), care is exercised to insure that the product is not heated since the N-hydroxy-2-azetidinone is susceptible to thermal rearrangement as described by T. Hirose, et al., *Heterocyclics*, 1982, 19, 1019.

The process of this invention are illustrated by the following reaction scheme.

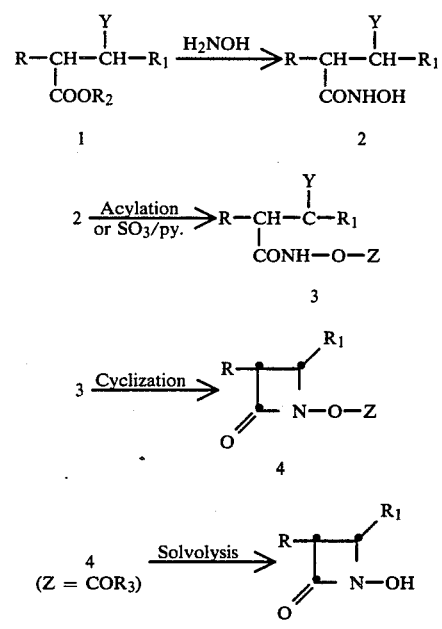

In a preferred embodiment of this invention R in the above formulae is a protected amino group. The protecting group of the protected amino group R can be any conventional amino protecting group stable under the conditions of the process as described hereinabove. For example, the protecting group can be an acyl group derived from a carboxylic acid (amide formation), or a group that forms a carbamate with the amino group. With respect to an acyl-protecting group, the acyl group can be selected for the purpose of temporary protection of the amino group or, alternatively, it can be selected because it is the desired side chain of the ultimate $\beta$-lactam antibiotic or $\beta$-lactamase inhibitor prepared with the N-hydroxy-2-azetidinone (5) or with the O-sulfo N-hydroxyazetidinone. Examples of acyl groups are C$_1$–C$_4$ alkanoyl such as formyl, acetyl, and propionyl; benzoyl and substituted benzoyl, eg. lower alkyl substituted benzoyl such as 4-methylbenzoyl, 2,4-dimethylbenzoyl, and 4-t-butylbenzoyl, halobenzoyl such as 4-chlorobenzoyl, 3,4-dichlorobenzoyl, 3-bromobenzoyl, and 4-fluorobenzoyl, lower alkoxy substituted benzoyl such as 4-methoxybenzoyl, 3-ethoxybenzoyl, and 2,6-dimethoxybenzoyl; arylalkanoyl, eg. phenylacetyl and substituted phenylacetyl such as 4-methylphenylacetyl, 4-methoxyphenylacetyl, 2,4-dimethoxyphenylacetyl, 3,4-dichlorophenylacetyl, 3-bromophenylacetyl, 2-fluorophenylacetyl, 4-cyanophenylacetyl, and 4-hydroxyphenylacetyl; α-substituted arylalkanoyl groups, eg. mandeloyl, phenylglycyl, malonyl, and such groups substituted on the phenyl ring by lower alkyl, lower alkoxy, halogen, cyano, or hydroxy, and where the α-amino, α-hydroxy, and α-carboxy groups thereof are suitably protected during the process of this invention; aryloxyalkanoyl and arylthioalkanoyl, eg. phenoxyacetyl, 4-chlorophenoxyacetyl, phenylmercaptoacetyl, 3,4-dichlorophenylmercaptoacetyl and 4-fluorophenylmercaptoacetyl; heteroarylalkanoyl groups, eg. thienylacetyl, acetyl, furylacetyl, thiazolylacetyl, oxazolylacetyl, 1,3,4-thiadiazolylacetyl, 1,3,4-oxadiazolylacetyl, 1,2,4-thiadiazolylacetyl, 1,2,4-oxadiazolylacetyl, and such groups wherein the hetero ring is substituted by amino, hydroxy, halogen, or methyl; α-substituted heteroaryl, eg. the above-mentioned heteroacetyl groups wherein the acetyl α-carbon is substituted by amino, hydroxy, carboxy, or an alkoxyimino group and wherein the amino, hydroxy, and carboxy groups are suitably protected during the process of this invention; and like acyl groups.

The protecting group also may be derived from a dicarboxylic acid, for example R may be the phthalimido group, the succinimido group and like diacylamido protecting groups.

An especially preferred amino protecting group is the so-called "Ox" protecting group, the 4,5-diphenyl-4-oxazolin-2-one group, shown below, formed with the amino group and 1,2-diphenylvinylene carbonate (J. C. Sheehan, et al. *J. Org. Chem.*, 18, No. 17, 3034–3040 [1973]).

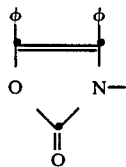

When in the above formulae the protecting group of the protected amino group R is a carbamate-forming protecting group, examples of such groups are represented by the formula

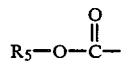

wherein R$_5$ is C$_1$–C$_5$ alkyl, halo-substituted alkyl, C$_3$–C$_5$ alkenyl, C$_3$–C$_6$ cycloalkyl, adamantyl, diphenylmethyl, benzyl, substituted benzyl substituted by methoxy, methyl, halogen, or nitro, or R$_5$ is a tertalkinyl group represented by the formula

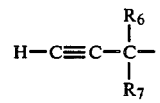

wherein R$_6$ and R$_7$ when taken separately are independently hydrogen or C$_1$–C$_3$ alkyl, and when taken together form a C$_5$–C$_7$ cycloalkyl group. Examples of such protecting groups are methoxycarbonyl, ethoxycarbonyl, isobutyloxycarbonyl, t-butyloxycarbonyl, t-amyloxycarbonyl, 2,2,2-trichloroethoxycarbonyl, allyloxycarbonyl, cyclopentyloxycarbonyl, cyclohexyloxycarbonyl, adamantyloxycarbonyl, benzyloxycarbonyl, 4-methoxybenzyloxycarbonyl, p-nitrobenzyloxycarbonyl, diphenylmethoxycarbonyl, dimethylethinylcarbinyloxycarbonyl, diethylethinylcarbinyloxycarbonyl, methylethylethinylcarbinyloxycarbonyl, 1-ethinylcyclopentyloxycarbonyl, and 1-ethinylcyclohexyloxycarbonyl.

A preferred amino-protecting group of this invention is the carbamate-forming group. An especially preferred group is represented when R$_5$ is benzyl or substituted benzyl.

The acylprotecting groups formed with monocarboxylic acids are less preferred, owing to the tendency of such groups to form oxazoline side products during the cyclization step of the process in competition with β-lactam ring formation. Such side products are represented by the formula

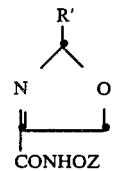

wherein R' is the organic residue of the acyl group and Z is as defined above.

Examples of N-acyloxy-3-(protected amino)-2-azetidinones represented by the formula 4 when R is an acylamino group are N-acetoxy-3-formamido-2-azetidinone, N-benzoyloxy-3-acetylamino-2-azetidinone, N-acetoxy-3-phenylacetylamino-4-methyl-2-azetidinone, N-acetoxy-3-phenylacetylamino-4-methyl-2-azetidinone, N-pivaloyloxy-3-phenoxyacetylamino-2-azetidinone, N-benzoyloxy-3-phenylacetylamino-4-ethoxycarbonyl-2-azetidinone, N-(4-chlorobenzoyloxy)-3-(2-thienylacetylamino)-2-azetidinone, N-butyryloxy-3-acetylamino-2-azetidinone, N-sulfooxy-3-phenylacetylamino-4-methyl-2-azetidinone, N-chloroacetoxy-3-phenoxyacetylamino-2-azetidinone, N-methoxyacetoxy-3-benzoylamino-4-methyl-2-azetidinone, N-propionoxy-3-(2,6-dimethoxybenzoylamino)-2-azetidinone, N-acetoxy-3-(p-methylbenzoylamino)-2-azetidinone, N-phenylacetoxy-3-phenoxyacetylamino-4-ethyl-2-azetidinone and N-acetoxy-3-[2-(2-aminothiazol-4-yl)-2-methoxyiminoacetamido]-3-methyl-2-azetidinone. Examples of compounds wherein R is a protected amino group formed with a dicarboxylic acid are N-acetoxy-3-phthalimido-3-ethyl-2-azetidinone and N-acetoxy-3-succinimido-2-azetidinone. Examples of N-acyloxy-2-azetidinones wherein R is the preferred Ox group are N-acetoxy-3-(4,5-diphenyl-4-oxazolin-2-one-3-yl)-2-azetidinone, N-benzoyloxy-3-(4,5-diphenyl-4-oxazolin-2-one-3-yl)-3-methyl-2-azetidinone, and N- acetoxy-3-(4,5-diphenyl-4-oxazolin-2-one-3-yl)-3-carboxy-2-azetidinone. When R is a carbamate amino-protecting group, examples of compound 4 are N-acetoxy-3-benzyloxycarbonylamino-2-azetidinone, N-benzoyloxy-3-(p-nitrobenzyloxycarbonylamino)-4-(p-nitrobenzyloxycarbonyl)-2-azetidinone, N-sulfooxy-3-(tert-butyloxycarbonylamino)-2-azetidinone, N-acetoxy-3-cyclohexyloxycarbonylamino-2-azetidinone, N-acetoxy-3-(dimethylethinylcarbinyloxycarbonylamino)-2-azetidinone, and N-acetoxy-3-adamantyloxycarbonylamino-4-phenyl-2-azetidinone.

In a preferred embodiment of this invention, N-benzyloxycarbonyl-L-serine methyl ester is reacted with hydroxylamine to form the hydroxamic acid and the latter is reacted with acetic anhydride to provide O-acetyl-N-benzyloxycarbonyl-L-serine hydroxamate. The O-acetyl derivative is reacted with triphenylphosphine, carbon tetrachloride and triethylamine to provide N-acetoxy-3-benzyloxycarbonylamino-2-azetidinone (Formula 4, R=Cbz, R$_1$=H, Z=COCH$_3$). Solvolysis of the N-acetoxy group of the 2-azetidinone in aqueous methyl alcohol with sodium carbonate provides N-hydroxy-3-benzyloxycarbonylamino-2-azetidinone (formula 5, R=Cbz, R$_1$=H).

In another preferred embodiment of this invention, N-Cbz-L-threonine methyl ester is converted to the hydroxamic acid, the hydroxamic acid is acylated with acetic anhydride, and the O-acetyl hydroxamate cyclized with TPP-CCl$_4$-TEA to provide N-acetoxy-3-Cbz-amino-4-methyl-2-azetidinone. Solvolysis of the acetyl group of the N-acetoxy-$\beta$-lactam gives N-hydroxy-3-Cbz-amino-4-methyl-2-azetidinone.

Preferred O-acylhydroxamates for use in the process are represented by the formula 3

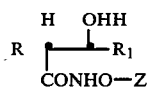

wherein R is benzyloxycarbonylamino, substituted benzyloxycarbonylamino or 4,5-diphenyl-4-oxazoline-2-one-3-yl; R$_1$ is hydrogen, methyl, C$_1$-C$_4$ alkoxycarbonyl, or protected carboxy; and Z is acetyl or benzoyl.

The above preferred O-acylhydroxamates in the designated configuration are prepared with the amino acids L-serine, L-threonine, and $\beta$-hydroxyaspartic acid by employing the procedures described hereinabove and selective blocking.

The N-hydroxy-2-azetidinones (5) provided by the process of this invention are useful intermediates to known antibiotic compounds. For example, the N-hydroxy compound (5) wherein R is an acylamino group is reacted with pyridine. SO$_3$ to provide the N-hydroxy-O-sulfated-2-azetidinones disclosed in U.S. Pat. No. 4,337,197 and represented by the general formula

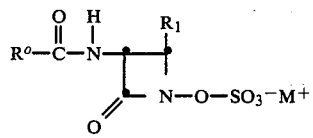

wherein R° is the residue of the carboxylic acids used to form the side chain acyl moieties described therein.

The above-described N-hydroxy-O-sulfated-2-azetidinones are also obtained directly by the cyclization of the intermediate 3 wherein Z is a sulfo group.

For example, Ox-protected threonine methyl ester is converted to the hydroxamic acid and the latter reacted with the pyridine —SO$_3$ complex to provide the Ox-protected O-sulfo hydroxamate represented by the formula

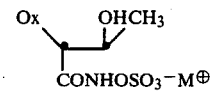

The hydroxamate is cyclized with TPP and diisopropylazodicarboxylate to provide the $\beta$-lactam.

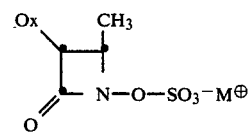

Removal of the Ox protecting group by catalytic hydrogenation over 5% Pd/C, and reacylation provides the desired 3-acylamino-N-hydroxy-O-sulfo-2-azetidinone. Alternatively, the N-hydroxy-2-azetidinones (5) can be reduced with titanium trichloride by the method described by P. G. Mattingly and M. J. Miller, *J. Org. Chem.*, 45, 410 (1980) to provide the N-unsubstituted azetidinone. The N-unsubstituted azetidinone obtained can be converted to nocardicin antibiotics as described by P. G. Mattingly and M. J. Miller, *J. Org. Chem.*, 46, 1557 (1981) or, alternatively, to monobactam-like antibiotics represented by the formula

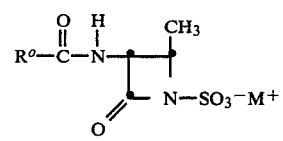

as described in U.K. Patent Application No. 2,071,650A published Sept. 23, 1981.

The preferred process of this invention employs a carbamate protected amino group or Ox protected amino group R and Z is acetyl or benzoyl. After the process is complete, the $\beta$-lactam 4 is subjected to solvolysis by the process of this invention and the protecting group is removed to provide the N-hydroxy-$\beta$-lactam nucleus represented by the formula wherein the nucleus is in zwitterionic form.

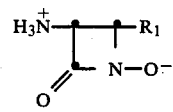

Alternatively, the amino-protecting carbamate group, e.g. the Cbz group, is removed by hydrogenation over 5% palladium-on-carbon prior to solvolysis of the O-acyl group to provide the N-acyloxy-3-amino-2-azetidinone. The aforementioned 3-amino-$\beta$-lactam compound may be acylated with an active derivative of the desired carboxylic acid to prepare the antibiotic compound or an intermediate thereof. Likewise, the protecting group of a 3-protected amino O-sulfo N-hydroxyazetidinone (Z=SO$_3^-$M$^+$) can be removed and the 3-amino nucleus acylated with the desired carboxylic acid.

As described above, in the process of this invention wherein R is a protected amino group of the type used for temporary protection of the amino group, the protecting group can be removed at any stage after the cyclization step and the amino group acylated with the desired carboxylic acid. A highly useful and convenient method for acylating the amino group of the β-lactam comprises the catalytic hydrogenolysis of a 3-benzyloxycarbonylamino-, or 3-substituted benzyloxycarbonylamino-N-acyloxy-2-azetidinone in the presence of the anhydride of the acid forming the desired side chain. For example, N-acetoxy-3-(Cbz-amino)-2-azetidinone is reduced with hydrogen in the presence of a supported palladium catalyst in an inert solvent containing in solution phenylacetic acid anhydride to provide, in one step, N-acetoxy-3-phenylacetylamino-2-azetidinone. The method is applicable to the acylation of 3-amino-β-lactam compounds where the desired acylamino moiety of the product does not itself contain a group which is reducible under the hydrogenolysis conditions described above. Examples of acids, the anhydrides of which can be used are acetic acid, benzoic acid, 2,6-dimethoxybenzoic acid, phenoxyacetic acid, thiophene-2-acetic acid, and like acids.

The process provided by this invention is characterized by the formation and cyclization of an acyclic O-acylhydroxamate. Prior to this invention the hydroxamate mediated approach to the synthesis of nocardicins [Mattingly and Miller, *J. Org. Chem.*, 46, 1557 (1981)] and monobactams [Floyd, et al., *J. Org. Chem.* 47, 176 (1982), and Cimarusti, et al., *J. Org. Chem.*, 47, 179 (1982)] required the preparation and use of O-substituted hydroxylamines, such as O-benzylhydroxylamine. Condensation of the O-substituted hydroxylamine with the β-hydroxy acid required the use of a carbodiimide and, since the cyclization of the O-substituted hydroxamate is most efficient at a controlled pH in aqueous media, the use of expensive water soluble carbodiimides was required. In addition, multiple chromatographies were employed. The present process comprises the simple, direct formation of a hydroxamic acid, the facile acylation thereof, and cyclization of the O-acyl derivative under mild conditions to the β-lactam. Further, the N-acyloxyazetidinone 4 is readily converted by facile hydrolysis to the useful N-hydroxy-2-azetidinone 5 by the process of this invention.

A further aspect of this invention provides compounds produced by the process described hereinabove which are represented by the following formula 6

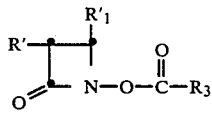

wherein
R' is amino, protected amino, hydrogen, $C_1$-$C_4$ alkyl, $C_1$-$C_4$ alkoxycarbonyl, protected carboxy, carboxy, or $C_1$-$C_4$ alkyl substituted by hydroxy, halogen, methoxy, amino, protected amino, carboxy, protected carboxy, or cyano;

R'$_1$ is hydrogen, $C_1$-$C_4$ alkyl, $C_1$-$C_4$ alkoxycarbonyl, protected carboxy, carboxy, phenyl, substituted phenyl substituted by $C_1$-$C_4$ alkyl, hydroxy, halogen, $C_1$-$C_4$ alkoxy, amino, protected amino, carboxy, protected carboxy, or cyano; or R'$_1$ is $C_1$-$C_4$ alkyl substituted by hydroxy, halogen, methoxy, amino, protected amino, carboxy, protected carboxy, or cyano; and R$_3$ is $C_1$-$C_{10}$ alkyl, $C_2$-$C_{10}$ alkenyl, $C_2$-$C_{10}$ alkinyl, phenyl, substituted phenyl substituted by $C_1$-$C_4$ alkyl, $C_1$-$C_4$ alkoxy, halogen, or nitro; $C_1$-$C_{10}$ alkyl substituted by halogen, carboxy, $C_1$-$C_4$ alkoxycarbonyl, $C_1$-$C_4$ alkylsulfonyl, nitro, $C_1$-$C_4$ alkoxy amino, phenyl or substituted phenyl as defined above.

The terms employed in the definition of the formula 6 have the same meanings as defined hereinabove for formula 4. Thus, "protected amino" refers to an acylamino group wherein the acyl portion is derived from a carboxylic acid and, also, to diacylamino groups. "Protected amino" also includes the amino group substituted by a protecting group conventionally employed for the temporary protection or blocking of the amino group.

A preferred protected amino group, R, is represented by the formula

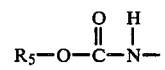

wherein R$_5$ has the same meanings as defined hereinabove. A further preferred protected amino group is the diphenyloxazolino group (Ox) represented by the formula

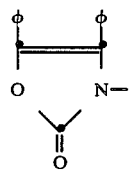

Preferred protected amino groups R, when R is acylamino, include the amino group substituted with the following acyl groups

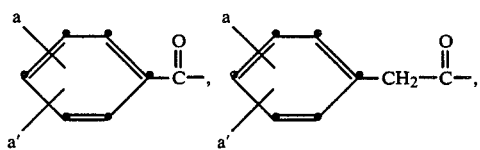

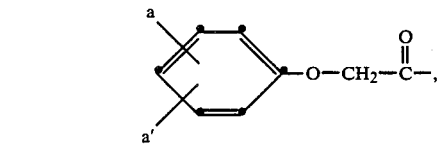

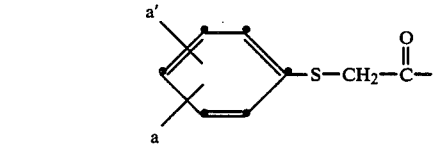

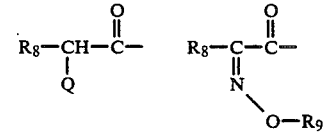

wherein a and a' are independently hydrogen, halogen, hydroxy, $C_1$-$C_4$ alkyl, $C_1$-$C_4$ alkoxy, or cyano; $R_8$ is phenyl, thienyl, furyl, thiazolyl, oxazolyl, 1,3,4-thiadiazolyl, 1,3,4-oxadiazolyl, 1,2,4-thiadiazolyl, 1,2,4-oxadiazolyl, and such heterocyclic rings substituted by amino, hydroxy, halogen, or methyl; Q is hydrogen, amino, hydroxy, carboxy, or methyl; and $R_9$ is $C_1$-$C_4$ alkyl, carboxymethyl, 1- or 2-carboxyethyl, or 2-carboxyprop-2-yl.

Examples of protected amino groups R when R is a diacylamino group include phthalimido and succinimido.

Preferred compounds are represented by the formula 6 when R is benzyloxycarbonylamino, p-nitrobenzyloxycarbonylamino, t-butyloxycarbonylamino, or the 4,5-diphenyl-4-oxazolin-2-one-3-yl group; $R_3$ is methyl, phenyl or substituted phenyl; and $R_1$ is hydrogen, $C_1$-$C_4$ alkyl, carboxy, protected carboxy, or $C_1$-$C_4$ alkoxycarbonyl.

The compounds represented by the formula 6, wherein a free amino group is present, form acid addition salts with organic and inorganic acids and such salts are included in this invention. Suitable acids for forming such salts include the mineral acids such as hydrochloric, hydrobromic, sulfuric, and phosphoric acids, the carboxylic acids such as acetic, propionic, chloroacetic, benzoic, toluic, citric, and tartaric, and the organosulfonic acids such as methanesulfonic, benzenesulfonic, toluenesulfonic, and naphthalenesulfonic acid.

Likewise, when in the formula 6 a free carboxy group is present, the compound may be in salt form such as an alkali metal, ammonium, or amine salt.

Examples of preferred compounds represented by the formula 6 are N-acetoxy-3-benzyloxycarbonylamino-2-azetidinone, N-acetoxy-3-benzyloxycarbonylamino-4-methyl-2-azetidinone, N-acetoxy-3-(4,5-diphenyl-4-oxazolin-2-one-3-yl)-2-azetidinone, N-acetoxy-3-amino-2-azetidinone, N-acetoxy-3-amino-4-methyl-2-azetidinone, N-benzoyloxy-3-amino-2-azetidinone, N-acetoxy-3-phenylacetylamino-2-azetidinone, N-acetoxy-3-phenoxyacetylamino-2-azetidinone, N-acetoxy-3-(2,6-dimethoxybenzoylamino)-2-azetidinone, N-acetoxy-3-(2-thienylacetylamino)-2-azetidinone, N-acetoxy-3-[2-(2-aminothiazol-4-yl)-syn-2-methoxyiminoacetylamino]-2-azetidinone, and N-benzoyloxy-3-[2-(2-aminothiazol-4-yl)-syn-2-methoxyiminoacetylamino]-4-methyl-2-azetidinone.

The following examples further illustrate the invention. In the examples all melting points were taken on a Thomas-Hoover melting point apparatus and are uncorrected. Infrared spectra were recorded on a Perkin-Elmer 727b spectrometer. $^1$HNMR spectra were obtained in chloroform-d with tetramethylsilane as a reference on Varian EM390, XL-100 or Nicolet NB300 spectrometers. Mass spectra were recorded on an AEI Scientific Apparatus 902 or Dupont DP102 spectrometer. Optical rotations were obtained using a Rudolf 574 polarimeter.

EXAMPLE 1

O-Acetyl-α-N-Cbz-L-serine hydroxamate

A solution of 1.27 g (ca 5 mmole) of α-N-Cbz-L-serine methyl ester in 10 ml of methyl alcohol was cooled in an ice bath. In separate flasks, 400 mg (5.76 mmole) of hydroxylamine hydrochloride and 0.7 g of potassium hydroxide were dissolved by warming in 10 ml portions of methyl alcohol. Both solutions were cooled to room temperature and the potassium hydroxide solution was added to the hydroxylamine hydrochloride solution. The mixed solutions immediately formed a precipitate of potassium chloride and the suspension was added to the cold solution of the serine methyl ester with stirring. After 5 minutes one drop of the reaction mixture was removed and added to a 1% aqueous ferric chloride solution. The immediate formation of a dark red color indicated formation of some of the hydroxamate. After 20 minutes, thin layer chromatography (ethyl acetate-silica gel) indicated that a small amount of starting material remained. The reaction was allowed to continue for a total time of 45 minutes after which 1 ml of acetic anhydride was added. After 10 minutes the reaction mixture was still positive to ferric chloride and an additional 0.1 ml of acetic anhydride was added. A ferric chloride test run immediately thereafter was negative. The reaction mixture was immediately poured into a separatory funnel containing 20 ml of 5% sodium carbonate and 50 ml of ethyl acetate. The aqueous layer was withdrawn and the organic layer was extracted twice with 15 ml portions of 5% sodium carbonate. The combined aqueous layers were placed in a separatory funnel over 25 ml of methylene chloride and acidified with swirling to a pH of ca. 4–5 by the dropwise addition of 6N hydrochloric acid. The layers were separated and the aqueous layer was extracted thrice with 25 ml portions of methylene chloride. The extracts were combined with the methylene chloride layer, washed with brine, dried over magnesium sulfate, filtered and evaporated to give 915 mg (63%) of O-acetyl-α-N-Cbz-L-serine hydroxamate as a white solid. Recrystallization from ethyl acetatehexanes gave an analytical sample melting at about 120°–121° C. (appeared to sinter at 110° C.–119° C.).

IR (KBr) 1700 cm$^{-1}$ (broad).

$^1$HNMR (CDCl$_3$, 90 MHz) 2.15 (s, 3H), 3.5–4.1 (m, 3H, OH+CH$_2$), 4.35 (m, 1H), 5.1 (s, 2H), 6.1 (br. d, NH), 7.33 (s, 5H).

Elemental analysis (percent) calculated for $C_{13}H_{16}O_6N_2$: Theory: C, 52.70; H, 5.44; N, 9.45. Found: C, 52.56; H, 5.71; N, 9.51.

EXAMPLE 2

N-Acetoxy-3-(Cbz-amino)-2-azetidinone

To a solution of 1.184 g (4 mmole) of the serine O-acetyl hydroxamate, obtained as described by Example 1, in 30 ml of dry acetonitrile containing 1 ml of carbon tetrachloride were added simultaneously 4.2 mmole of triphenylphosphine (TPP) and 4.4 mmole of triethylamine. The reaction mixture was stirred at room temperature under a drying tube and was monitored by thin layer chromatography (ethyl acetate-silica gel, product $R_f$ ca. 0.6). After 8 hours the TPP ($R_f$ ca. 0.7) was nearly depleted and the reaction mixture was concentrated to a volume of 2–3 ml. The concentrate was applied to a small Michael-Miller column of silica gel (40–63μ) and the column eluted with ethyl acetatehexanes at 30 ml/min. Several UV active fractions containing the desired product were obtained. The fractions containing the product were combined and evaporated to dryness to give 734 mg (66%) of N-acetoxy-3-(Cbz-amino)-2-azetidinone as a white solid. Recrystallization from ethyl acetate-hexanes gave an analytical sample melting at about 130° C. to about 131° C.

IR (KBr) 3350 (broad), 1820, 1710 cm$^{-1}$.

¹HNMR (90 MHz) 2.13 (s, 3H), 3.53 (dd, 1H), 3.95 (dd, apparent t, 1H), 4.8 (m, 1H), 5.1 (s, 2H), 5.7 (d, NH), and 7.33 (s, 5H) δ.

Elemental analysis (percent) calculated for $C_{13}H_{14}N_2O_5$: Theory: C, 56.11; H, 5.07; N, 10.06. Found: C, 55.86; H, 5.21; N, 10.04.

EXAMPLE 3

N-Hydroxy-3-(Cbz-amino)-2-azetidinone

A cold (0° C.) suspension of 139 mg (0.5 mmole) of the N-acetoxyazetidinone, obtained as described by Example 2, in 8 ml of methyl alcohol-water (2:1, v:v) were added with vigorous stirring 135 mg (1.25 mmole) of solid sodium carbonate. After 15 minutes an aliquot of the reaction mixture was removed and analyzed via thin layer chromatography (ethyl acetate on silica gel). Two spots on the chromatogram showed starting material ($R_f$ 0.6) and product ($R_f$ 0.2–0.3). After 30–45 minutes the starting material was no longer visible on TLC chromatograms. The apparent pH of the reaction mixture was adjusted to pH 5 with 1.0N hydrochloric acid. The mixture was extracted four times with fresh 25 ml portions of ethyl acetate. The extracts were combined, washed with brine, dried over magnesium sulfate, filtered, and evaporated to dryness to give 101 mg (85.6%) of N-hydroxy-3-(Cbz-amino)-2-azetidinone as a white solid melting at about 149° C. to about 150° C. d.

IR (KBr) 3250 (broad), 1780, 1740, and 1700 cm$^{-1}$.

¹HNMR (90 MHz in acetone-$D_6$) 3.3 (dd, 1H), 3.64 (apparent t, 1H), 4.50 (m, 1H), 4.97 (s, 2H), 6.97 (m, 1H), and 7.33 (s, 5H) 67.

¹HNMR (90 MHz in DMSO-$D_6$) 3.35 (dd, 1H), 3.7 (apparent t, 1H), 4.5 (m, 1H), 5.1 (s, 2H), 7.4 (s, 5H), 8.05 (br. d, NH), and 10.3 (br. OH) δ.

Elemental analysis (percent) calculated for $C_{11}H_{12}N_2O_4$: Theory: C, 55.92; H, 5.12; N, 11.85. Found: C, 55.89; H, 5.34; N, 11.67.

EXAMPLE 4

α-N-Phenylacetyl-L-serine hydroxamic acid

A solution of 2.03 g (29.2 mmole) of hydroxylamine hydrochloride in 10 ml of methyl alcohol was treated with a solution of 3.3 g of potassium hydroxide in 15 ml of methyl alcohol with the immediate formation of a suspension (KCl precipitate). The suspension was cooled in an ice bath and then added with stirring to a cold solution of 4.52 g (19.5 mmole) of N-phenylacetyl-α-serine methyl ester in 30 ml of methyl alcohol. After 1.5 hours the reaction mixture was filtered and concentrated by evaporation to a volume of 25 ml. The concentrate was diluted with 10 ml of water and then was acidified to an apparent pH of 3 with 6 N hydrochloric acid. The acidified mixture was cooled in an ice bath and the α-N-phenylacetyl-L-serine hydroxamic acid crystallized. The product was recrystallized from ethyl alcohol-diethyl ether to give 3.06 g (67%) of analytically pure product melting at about 169.5° C. to about 171° C. d.

IR (KBr) 3205 cm$^{-1}$, 1630 cm$^{-1}$.

¹HNMR (90 MHz, CDCl$_3$+CD$_3$OD) 3.61 (s, 2H), 3.74 (d, 2H), 4.38 (m, 1H), and 7.32 (s, 5H) δ.

Elemental analysis (percent) calculated for $C_{11}H_{14}N_2O_4$:
Theory: C, 55.46; H, 5.92; N, 11.76.
Found: C, 55.37; H, 6.10; N, 11.78.

EXAMPLE 5

O-Benzoyl-α-N-phenylacetylserine hydroxamate

To a solution of 0.497 g (2.09 mmole) of the serine hydroxamic acid, prepared as described by Example 4, in 35 ml of methyl alcohol and containing 0.32 ml (2.3 mmole) of triethylamine was added dropwise at room temperature with stirring 0.242 ml (2.085 mmole) of benzoyl chloride. After stirring for 10 minutes the reaction mixture gave a negative ferric chloride test and was poured into a separatory funnel containing 125 ml of ethyl acetate and 20 ml of water. The layers were separated and the organic layer was washed once with 10 ml of water, dried over magnesium sulfate, filtered and evaporated to dryness to give O-benzoyl-α-N-phenylacetylserine hydroxamate as a white solid. The white solid was recrystallized from ethyl acetate-hexanes to provide 0.628 g (88%) of the product melting at about 137° C. to about 139° C.

IR (KBr) 1760 and 1640 cm$^{-1}$.

¹HNMR (CDCl$_3$+CD$_4$OD) 3.66 (s, 2H), 3.89 (d, 2H), 4.65 (1H, partially obscured by OH peak), 7.34 (s, 5H), 7.63 (m, 3H), and 8.14 (m, 2H) δ.

EXAMPLE 6

N-Benzoyloxy-3-(phenylacetylamino)-2-azetidinone

A solution of 0.31 g (0.89 mmole) of the O-benzoyl serine hydroxamate, prepared as described by Example 5, 0.26 g (0.99 mmole) of triphenylphosphine and 0.193 ml of diisopropyldiazodicarboxylate in 25 ml of tetrahydrofuran was stirred for 1 hour at room temperature under nitrogen. The reaction mixture was evaporated to dryness to a yellow oil. The oil was chromatographed over silica gel using ethyl acetate-hexanes (1:1, v:v) for elution to give N-benzoyloxy-3-(phenylacetylamino)-2-azetidinone and the oxazoline, O-benzoyl-2-benzyloxazolino-4-hydroxamate in 65% yield in a ratio of 1:5. The desired azetidinone product was recrystallized from ethyl acetate-hexanes to provide the purified product in 6% yield melting at about 127.5° C. to about 130° C.

IR (KBr) 1795, 1760, and 1650 cm$^{-1}$.

¹HNMR (CDCl$_3$) 3.65 (s, 2H), 3.72 (m, 1H), 4.15 (m, 1H), 5.15 (m, 1H), 6.10 (m, 1H), and 7.26–8.04 (m, 1H).

EXAMPLE 7

N-Hydroxy-3-phenylacetamido-2-azetidinone

The N-benzoyloxy-3-(phenylacetylamino)-2-azetidinone is subjected to solvolysis with sodium carbonate in aqueous methyl alcohol by following the conditions described by Example 3 to provide the title compound.

EXAMPLE 8

One-step conversion of N-acetoxy-3-(Cbz-amino)-2-azetidinone to N-acetoxy-3-(phenylacetylamino)-2-azetidinone To a solution of 28 mg (0.1 mmole) of N-acetoxy-3-(Cbz-amino)-2-azetidinone, prepared as described by Example 2, in 8 ml of ethyl acetate under nitrogen were added 25 mg of 5% palladium on carbon and 25.5 mg (0.1 mmole) of phenylacetic anhydride. Hydrogen was passed slowly over the stirred solution for 2 hours at room temperature. The catalyst was filtered and washed with 20 ml of ethyl acetate. The wash was combined with the filtrate and the whole extracted with 25 ml of 5% sodium bicarbonate to remove the phenylacetic acid. The organic layer was washed with 20 ml of brine, dried over magnesium sulfate, filtered and evaporated to provide 25 mg of N-acetoxy-3-(phenylacetylamino)-2-azetidinone as a white solid. The white solid was recrystallized from ethyl acetate-hexanes to provide the purified product melting at about 147° C. to about 149° C. Rf [silica gel with ethyl acetate-hexanes (8:2, v:v)]=0.5.

$^1$HNMR (CDCl$_3$) 2.10 (s, 3H), 3.56 (broad s, 3H), 3.96 (apparent t, 1H), 4.92 (m, 1H), 6.92 (broad d, NH), and 7.33 (s, 5H) δ.

Mass spectrum (FD) m/e 263 (M+1).

EXAMPLE 9

3-(Cbz-Amino)-2-azetidinone

A solution of 118 mg (0.5 mmole) of N-hydroxy-3-(Cbz-amino)-2-azetidinone, prepared as described by Example 3, in 10 ml of tetrahydrofuran and 10 ml of water at pH 7 was added to a flask equipped with a magnetic stirrer, a buret, and a pH electrode. The solution was maintained under nitrogen and was treated with a solution of 0.8 ml of 20% titanium trichloride by dropwise addition from a syringe. The pH of the reaction mixture was maintained at 7.0 during the addition of the TiCl$_3$ by the addition of 3.0 N sodium hydroxide through the buret as needed. After the addition was complete the reaction mixture was stirred at room temperature for 2 hours. The pH of the reaction mixture was adjusted to 8.0, transferred to a separatory funnel and extracted with three 25 ml portions of ethyl acetate. The combined ethyl acetate was washed with 10 ml of brine, dried over magnesium sulfate, filtered and evaporated to dryness. The residue was recrystallized from ethyl acetate-hexanes to give 69 mg (60%) of 3-(Cbz-amino)-2-azetidinone as a white solid melting at about 160° C. to about 161° C.

IR (KBr) 1740, 1700 cm$^{-1}$.

$^1$HNMR (acetone d$_6$) 2.86 (m, H), 3.23 (dd, 1H), 3.46 (apparent t, 1H), 4.8 (m, 1H), 5.07 (s, 2H), 7.0 (m, 1H), 7.36 (s, 5H).

EXAMPLE 10

2-Oxo-3-(Cbz-amino)-1-azetidinyl sulfate tetra-n-butyl ammonium salt

To 2 ml of pyridine containing 200 mg (0.125 mmole) of pyridine.SO$_3$ were added 100 mg (0.423 mmole) of N-hydroxy-3-(Cbz-amino)-2-azetidinone and the suspension was stirred for 6 hours at room temperature. The pyridine was evaporated and the residue was dissolved in 50 ml of 0.5 M potassium dihydrogen phosphate. The solution was washed with three 20 ml portions of ethyl acetate to remove organic soluble impurities. To the solution were added 108 mg (0.317 mmole) of tetrabutylammonium hydrogen sulfate and the solution was extracted with four 60 ml portions of methylene chloride. The extracts were combined, dried over magnesium sulfate, filtered and evaporated to give 150 mg (70%) of the title compound as a thick oil.

$^1$HNMR (CDCl$_3$) (m, 12H), 1.53 (m, 16H), 3.23 (m, 8H), 3.74 (dd, 1H), 4.1 (apparent t, 1H), 4.76 (m, 1H), 5.1 (s, 2H), 6.17 (br. d, 1H), and 7.4 (s, 5H) δ.

EXAMPLE 11

3-Amino-N-hydroxy-2-azetidinone

A solution of 236 mg (1 mmole) of N-hydroxy-3-(Cbz-amino)-2-azetidinone in 15 ml of tetrahydrofuran:water (1:1) was flushed with nitrogen and 15 mg of 5% palladium-on-carbon were added. Hydrogen was bubbled through the suspension for 1 hour at room temperature after which no UV active spots were visible on thin layer analysis of the reduction mixture. The catalyst was removed by filtration and the filtrate evaporated to remove THF. The aqueous concentrate was lyophilized to give 99 mg (99%) of 3-amino-N-hydroxy-2-azetidinone as a white solid which decomposed at 250° C. to a dark brown solid. The product gives a positive ferric chloride test in methyl alcohol and is ninhydrin positive. Titration indicated pK values of 5.2 and 7.2.

IR (KBr) 3550 (broad), 1740, 1640 cm$^{-1}$.

$^1$HNMR (D$_2$) 3.5 (dd, 1H), 3.87 (apparent t, 1H), and 4.27 (m, 1H) 6.

EXAMPLE 12

2-Oxo-3-phenylacetylamino-1-azetidinyl sulfate tetra-n-butylammonium salt

A solution of N-phenylacetyl serine hydroxamate (0.31757 g, 1.3321 mmole) in about 8 ml of dry pyridine was stirred with about 0.5 ml of 4A molecular sieves. The pyridine.SO$_3$ complex (0.23416 g, 1.4712 mmole) was added and the mixture stirred under nitrogen for 24 hours. The reaction mixture was evaporated to provide the acyclic O-sulfated hydroxamate as a yellow oil. The oil is poured into a large excess of 0.5 M potassium dihydrogenphosphate and the solution is washed once with ethyl acetate. Tetra-n-butylammonium hydrogen sulfate (1:5 equiv.) is then added to the washed solution with stirring. The aqueous layer is extracted with methylene chloride and then dried and evaporated to provide the acyclic O-sulfated hydroxamate tetra-n-butylammonium salt.

The acyclic tetra-n-butylammonium salt is cyclized in acetonitrile or THF under anhydrous conditions with TPP-diethylazodicarboxylate to provide the title compound.

EXAMPLE 13

N-Phenylacetyl serine hydroxamate O-sulfo potassium salt

N-Phenylacetyl serine hydroxamate (0.3175 g, 1.3321 mmole) is dissolved in about 8 ml of dry pyridine and the solution is stirred with about 0.5 ml of 4A molecular sieves. Pyridine.SO$_3$ complex (1.1 eg.) was added and the mixture stirred under nitrogen for 24 hours. The reaction mixture was evaporated and the product, obtained as a yellow oil, failed to crystallize from ethanol or acetonitrile. The oil was dissolved in about 2 ml of water, the solution passed through a Dowex sulfonic acid resin (K$^+$ form), and the resin eluted with water. The UV active fractions were combined and lyophilized to provide 0.36984 g (78%) of the product as a tan powder.

m.p. dec. >130° C.

IR: 1650, 1500, 1220–1240, 1110 cm$^{-1}$.

NMR (d$_6$ DMSO) 3.30 (m, 2H), 3.50 (s, 2H), 3.89 (m, 1H), 4.34 (m, 1H), 7.30 (s, 5H), and 8.28 (m, 1H) δ.

I claim:

1. A compound of the formula

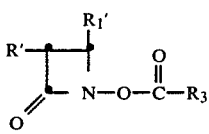

wherein R' is amino, hydrogen, $C_1$–$C_4$ alkyl, carboxy, protected carboxy, $C_1$–$C_4$ alkyl mono-substituted by hydroxy, halogen, methoxy, amino, protected amino, carboxy, protected carboxy, or cyano; or R' is an acylamino group of the formulae

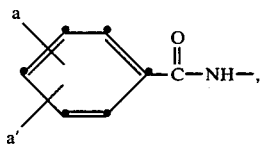

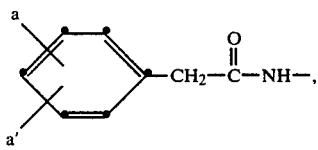

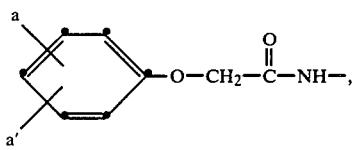

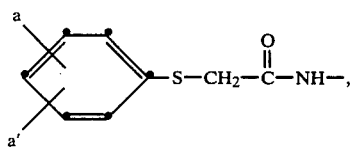

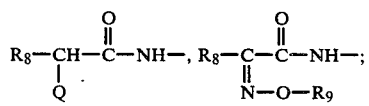

or a protected amino group selected from a group of the formula

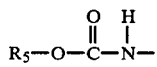

wherein $R_5$ is $C_1$–$C_5$ alkyl, halo-substituted alkyl, $C_3$–$C_5$ alkenyl, $C_3$–$C_6$ cycloalkyl, adamantyl, diphenylmethyl, benzyl, substituted benzyl substituted by methoxy, methyl, halogen, or nitro; or $R_5$ is an alkinyl group of the formula

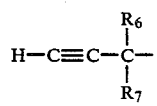

wherein $R_6$ and $R_7$ when taken separately are independently hydrogen, or $C_1$–$C_3$ alkyl, and when taken together with the carbon to which they are attached form a $C_5$–$C_7$ cycloalkyl group; or R' is a diphenyloxazolino group of the formula

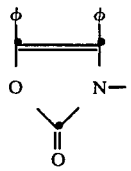

wherein $\phi$ is phenyl; and where in the above R' acylamino groups, a and a' are independently hydrogen, halogeny, hydroxy, $C_1$–$C_4$ alkyl, $C_1$–$C_4$ alkoxy, or cyano; $R_8$ is phenyl, thienyl, furyl, thiazolyl, oxazolyl, 1,3,4-thiadiazolyl, 1,2,4-oxadiazolyl, and such heterocyclic rings mono-substituted by amino, hydroxy, halogen, or methyl; Q is hydrogen, amino, hydroxy, carboxy, or methyl; and $R_9$ is $C_1$–$C_4$ alkyl, carboxymethyl, 1- or 2-carboxyethyl, or 2-carboxyprop-2-yl;

$R'_1$ is hydrogen, $C_1$–$C_4$ alkyl, protected carboxy, carboxy, phenyl, substituted phenyl substituted by $C_1$–$C_4$ alkyl, hydroxy, halogen, $C_1$–$C_4$ alkoxy, amino, protected amino, carboxy, protected carboxy, or cyano; or $R'_1$ is $C_1$–$C_4$ alkyl, mono-substituted by hydroxy, halogen, methoxy, amino, protected amino, carboxy, protected carboxy, or cyano; and $R_3$ is methyl, phenyl, or substituted phenyl substituted by $C_1$–$C_4$ alkyl, $C_1$–$C_4$ alkoxy, halogen, or nitro; and when $R'_1$ is $C_1$–$C_4$ alkyl substituted by amino, or Q is amino, the acid addition salts thereof.

2. The compound of claim 1 wherein the protected amino group is

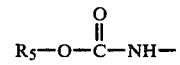

wherein $R_5$ is $C_1$–$C_5$ alkyl, halo-substituted alkyl, $C_3$–$C_5$ alkenyl, $C_3$–$C_6$ cycloalkyl, adamantyl, diphenylmethyl, benzyl, substituted benzyl substituted by methoxy, methyl, halogen, or nitro; or $R_5$ is an alkinyl group of the formula

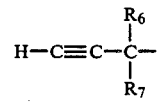

wherein $R_6$ and $R_7$ when taken separately are independently $C_1$–$C_3$ alkyl, and when taken together form a $C_5$–$C_7$ cycloalkyl ring.

3. The compound of claim 2 wherein $R_5$ is diphenylmethyl, benzyl, substituted benzyl, or $C_1$–$C_5$ alkyl.

4. The compound of claim 3 wherein $R_3$ is methyl, phenyl, or substituted phenyl and $R_1'$ is hydrogen, $C_1$–$C_4$ alkyl, carboxy, or protected carboxy.

5. The compound of claim 4 of the formula

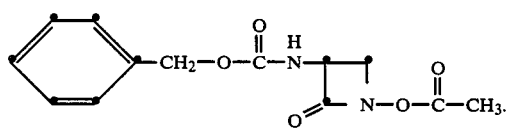

6. The compound of claim 1 wherein R' is amino; $R_3$ is methyl, phenyl, or substituted phenyl; $R_1'$ is hydrogen, methyl, or protected carboxy; and the acid addition salts thereof.

7. The compound of claim 1 wherein R' is an acylamino group of the formulae

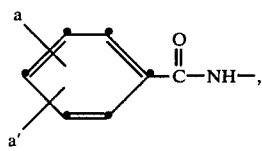

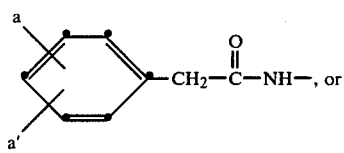

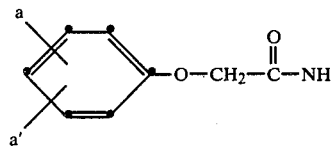

8. The compound of claim 7 wherein $R_3$ is methyl, phenyl, or substituted phenyl, and $R_1'$ is hydrogen, $C_1$-$C_4$ alkyl, carboxy, or protected carboxy.

9. The compound of claim 8 of the formula

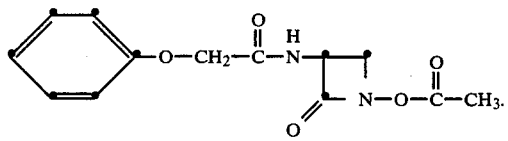

10. The compound of claim 8 of the formula

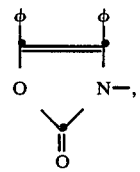

11. The compound of claim 1 wherein the protected amino group has the formula $R_3$ is methyl, phenyl, or substituted phenyl.

12. The compound of claim 11 of the formula

* * * * *